US00PP18535P2

(12) United States Plant Patent
Valstar

(10) Patent No.: US PP18,535 P2
(45) Date of Patent: Mar. 4, 2008

(54) ***CALATHEA* PLANT NAMED 'HGV08'**

(50) Latin Name: *Calathea hybrida*
Varietal Denomination: HGV08

(75) Inventor: Oscar Valstar, Maasland (NL)

(73) Assignee: Gebr. Valstar Beheer BV, Maasland (NL)

( * ) Notice: Subject to any disclaimer, the term of this patent is extended or adjusted under 35 U.S.C. 154(b) by 0 days.

(21) Appl. No.: 11/478,054

(22) Filed: Jun. 29, 2006

(51) Int. Cl.
*A01H 5/00* (2006.01)

(52) U.S. Cl. ..... Plt./375
(58) Field of Classification Search ..... Plt./375
See application file for complete search history.

*Primary Examiner*—Kent Bell
*Assistant Examiner*—S. B. McCormick-Ewoldt

(57) ABSTRACT

A new cultivar of *Calathea* plant named 'HGV08' that is characterized by ovate leaves that have a purple under side and a yellow-green upper side with dark green areas along the veins and margins and pink stripes between the secondary veins.

1 Drawing Sheet

Botanical classification: *Calathea hybrida.*
Variety denomination: 'HGV08'.

BACKGROUND OF THE INVENTION

The present invention relates to a new and distinct cultivar of *Calathea* plant botanically known as *Calathea hybrida* and hereinafter referred to by the cultivar name 'HGV08'.

The new cultivar was discovered and selected as a single plant by the inventor in a cultivated area of Maasland, The Netherlands in 2001. 'HGV08' was discovered as a naturally occurring whole plant mutation within a population of unnamed *Calathea* plants.

Asexual reproduction by division of the new cultivar 'HGV08' was first performed in 2001 in Maasland, The Netherlands. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Calathea* cultivar 'HGV08'.

1. *Calathea* 'HGV08' exhibits leaves that have a purple under side.
2. *Calathea* 'HGV08' exhibits leaves that have a yellow-green upper side with dark green areas along the veins and margins and pink stripes between the secondary veins.
3. *Calathea* 'HGV08' exhibits large ovate leaves.

The closest comparison cultivars are *Calathea* 'Concept' (not patented) and 'Wilson's Princep' (not patented). The new cultivar 'HGV08' is distinguishable from 'Concept' by the following characteristics:

1. 'HGV08' has leaves with larger yellow-green areas than 'Concept'.
2. 'HGV08' has leaves with pink stripes.

The new cultivar 'HGV08' is distinguishable from 'Wilson's Princep' by the following characteristics:

1. 'HGV08' has darker margins than 'Wilson's Princep'.
2. 'HGV08' has leaves with pink stripes.

BRIEF DESCRIPTION OF THE DRAWING

The accompanying photograph illustrates the distinguishing traits of *Calathea* 'HGV08'. The plant in the photograph shows an overall view of a 4 month old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Calathea* cultivar named 'HGV08'. Data was collected in Maasland, The Netherlands from 4 month old greenhouse grown plants in 13 cm containers. The time of year was Winter and the average temperature was 20 degrees Centigrade during the day and 18 degrees Centigrade at night. No photoperiodic treatments or growth retardants were used. Color determinations are in accordance with The Royal Horticultural Society Colour Chart 2001 edition, except where general color terms of ordinary dictionary significance are used. The growing requirements are similar to the species. 'HGV08' has not been tested under all possible conditions and phenotypic differences may be observed with variations in environmental, climatic, and cultural conditions, however, without any variance in genotype.

Botanical classification: *Calathea* 'HGV08'.
Use: Ornamental.
Parentage: 'HGV08' is a naturally occurring whole plant mutation of an unknown *Calathea* cultivar.
Vigor: Moderate.
Growth rate: Moderate.
Growth habit: Moderately branching from base.
Plant shape: Narrow inverted triangle.
Suitable container size: 13 cm diameter container.
Height: Average 28.5 cm in height.
Width: Average 38.3 cm in width.
Heat tolerance: Tolerant to 30 degrees Centigrade.
Winter hardiness: USDA Zone 10.
Propagation: Division.
Number of divisions or clumps per year: 3.

Time to produce a young plant: Approximately 30 days in the Summer and 45 days in the Winter.

Root system: Thick and fibrous.

Stem: No stems, Leaves grow directly from base, Average 7 clumps.

Foliage:

*Texture.*—Smooth, glossy both surfaces.

*Leaf arrangement.*—Alternate.

*Compound or single.*—Single.

*Leaf shape.*—Narrow Ovate to Ovate.

*Leaf apex.*—Short apiculate.

*Leaf base.*—Short attenuate.

*Leaf length.*—Average 17.1 cm in length.

*Leaf width.*—7.5 cm in width.

*Quantity of leaves per clump.*—Average 6.

*Pubescence.*—Absent.

*Leaf margin.*—Entire, wavy, average 12 waves per leaf.

*Vein pattern.*—Pinnate.

*Young leaf color* (*upper surface*).—144B with margins and narrow areas along veins 139A, pink stripes between secondary veins 37A and 37C with an average width of 1.5 mm.

*Young leaf color* (*lower surface*).—N77A.

*Mature leaf color* (*upper surface*).—144A with margins and narrow areas along veins between 136A and 139A, pink stripes between secondary veins 37A and 37C with an average width of 1.5 mm.

*Mature leaf color* (*lower surface*).—N77A.

*Vein color* (*lower surface*).—147C and 147D.

*Vein color* (*upper surface*).—143C.

*Leaf attachment.*—Petiolate.

*Petiole dimensions.*—Average 14.5 cm in length including geniculum, 3.5 mm in diameter below geniculum to 4 mm in diameter above clump.

*Petiole aspect.*—Round.

*Petiole surface.*—Smooth, glossy.

*Petiole color.*—147A, lighter toward the base 146C and 146D.

*Geniculum dimensions.*—Average 1.5 cm in length and 3.0 mm in diameter.

*Geniculum color.*—146A.

*Wing dimensions.*—Average 10.3 cm in length and 4 mm in diameter.

*Wing color.*—N77C.

*Durability of foliage to stress.*—Moderate to high.

Flowers: Flowers have not been observed.

Disease and insect resistance: Plants of the new *Calathea* have not been observed for disease or insect resistance.

It is claimed:

1. A new and distinct variety of *Calathea* plant named 'HGV08' as described and illustrated.

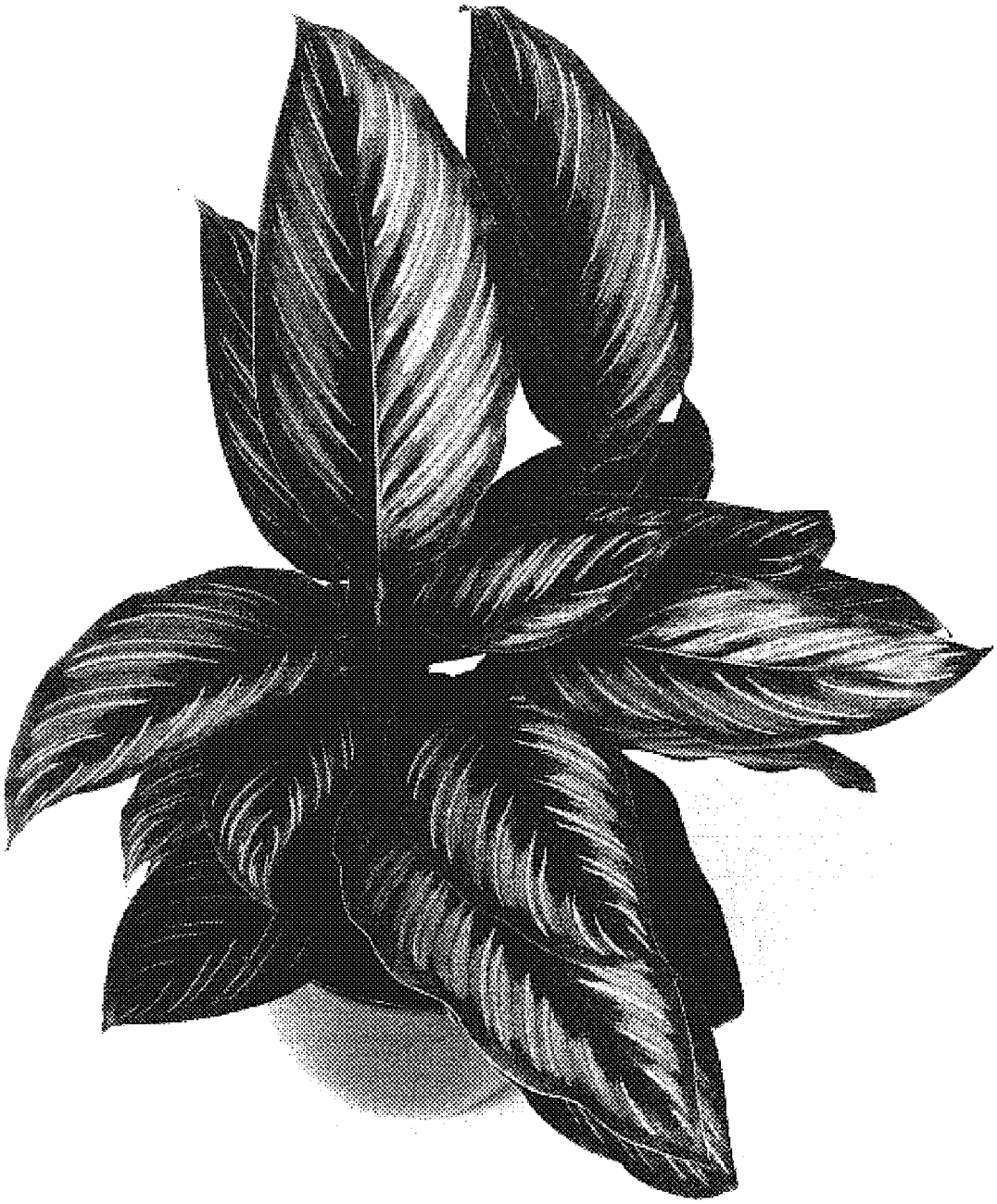

* * * * *